United States Patent [19]

Orlando et al.

[11] 4,374,201
[45] Feb. 15, 1983

[54] PROCESS FOR COATING A DRY VARIOLA VIRUS

[75] Inventors: Michael D. Orlando; Jean M. Riley, both of Frederick, Md.

[73] Assignee: The United States of America as represented by the Secretary of the Army, Washington, D.C.

[21] Appl. No.: 471,792

[22] Filed: Jul. 9, 1965

[51] Int. Cl.³ .............................................. C12N 5/00
[52] U.S. Cl. .................................. 435/239; 435/235; 435/260; 435/948; 89/1 A
[58] Field of Search ....................... 167/78, 78.5, 78.2, 167/54, 82, 83; 117/100, 141; 106/2; 435/239, 235, 260, 948; 89/1 A

[56] References Cited

U.S. PATENT DOCUMENTS 2,369,218  2/1945  Dick et al. ........................ 167/78.2
3,214,340  10/1965  Laurence ......................... 167/78.2

OTHER PUBLICATIONS

"Vaccination of Poultry", 1956; pp. 1–6.

Primary Examiner—Stephen J. Lechert, Jr.
Attorney, Agent, or Firm—Nathan Edelberg; Robert P. Gibson; Muzio B. Roberto

[57] ABSTRACT

A method of coating a dry variola virus obtained by the inoculation of the embryo of chicken eggs and stabilized by the addition of lactose, raffinose, lysine, sodium glutamate, isoniazid, and thiourea by treatment with methyl amyl acetate.

2 Claims, 1 Drawing Figure

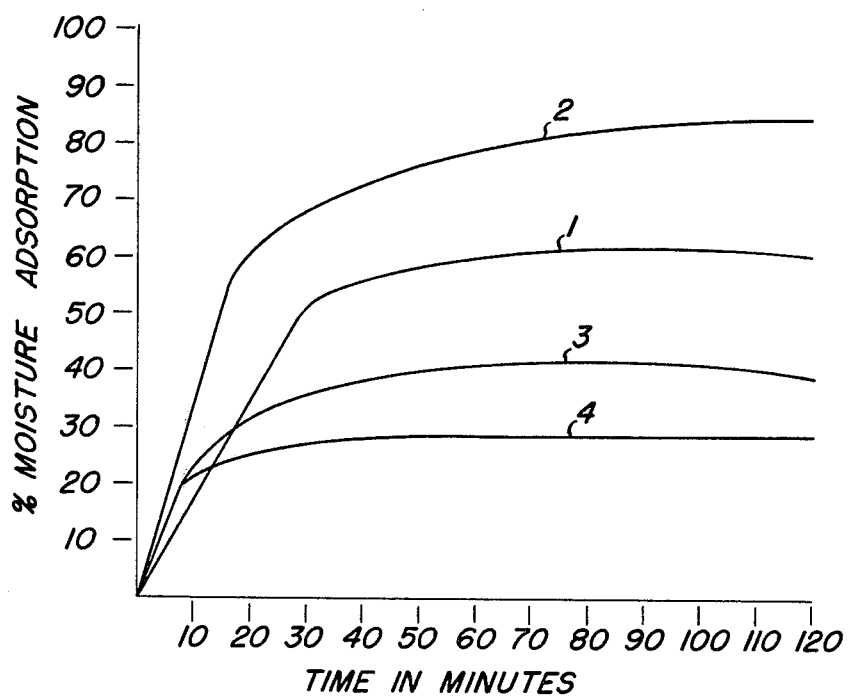

PROCESS FOR COATING A DRY VARIOLA VIRUS

The invention described herein may be manufactured and used by or for the Government of the United States of America for governmental purposes without the payment to us of any royalty thereon.

This invention relates to a method of coating a dry variola virus. More specifically it relates to a method of coating a dry variola virus, obtained by the inoculation of the embryo of chicken eggs, by the treatment thereof with a hydrophobous compound.

In co-pending application, Ser. No. 471,791, filed July 9, 1965, there is disclosed a method for the preparation of a variola virus comprising the inoculation of the chorioallantoic membranes, trysinization, stabilization and homogenization, purification by differential centrifugation and freeze drying the concentrated virus. However, the dried variola virus had a tendency to absorb moisture when exposed to an atmosphere having a relatively high humidity for an extended period of time.

It is an objective of this invention to provide for and disclose a method for the production of a variola virus having a high number of pock infectious units per gram of material.

It is a further object of the invention to provide for and disclose a method for coating the dry variola virus thereby decreasing the tendency thereof to absorb water when exposed to an atmosphere having a high relative humidity for an extended period of time.

Specifically, 11 day embryonated, non-disinfected eggs containing areas of well developed chorioallantoic membrane devoid of large blood vessels are selected. Three holes were drilled through the shells (one hole over the center of the air space and two holes over the selected chorioallantoic membrane area). An artificial air space is created by applying a vacuum to the hole drilled over the center of the air space and making a tiny hole in the fibers of the membrane covering the hole over the chorioallantoic area which in turn drops the chorioallantoic membrane. The egg is now rotated so that the chorioallantoic membrane is directly beneath the second hole.

A secondary seed of a variola virus prepared as described in the co-pending application was utilized to inoculate the dropped chorioallantoic membrane utilizing a one milliliter tuberculin syringe. The inoculated eggs are rolled slightly to insure distribution of the inoculum over the exposed chorioallantoic membrane. The unsealed eggs are then placed on their long axis in trays with the dropped chorioallantoic membrane facing upwards and incubated at around 35° C. for 66 hours.

The infected chorioallantoic membranes are harvested by cutting the egg in half along the long axis and detaching thereof.

An 80% suspension of the chorioallantoic membrane in aqueous solution is prepared in a stabilizer comprising: 0.5 to 2.0% lactose, 0.5 to 2.0% raffinose, 0.3 to 1.2% lysine, 0.3 to 1.2% sodium glutamate, 0.1 to 0.4% isoniazid and 0.1 to 0.4% thiourea. The resultant mixture is agitated for a period of 5 minutes and then centrifuged lightly (1000 g) for 3 minutes to remove particulates. The supernatant containing the virus is frozen as pellets on a modified drum pelleter at a temperature of around −40° C.

The frozen pellets are placed in 15 milliliter vaccine vials and inserted into the platen of a waffle iron dryer. The platen had been previously cooled to a temperature of around −20° C. The drying chamber is evacuated to a pressure of around 400 microns of mercury and the pressure held there for several hours. The temperature of the platen holding the vials was raised to 40° C. as soon as possible after the operating pressure was reached. This temperature is maintained during the entire drying. At the end of the seven hour period, the vials are stoppered while under vacuum, removed from the dryer and held in storage at a temperature of −18° C.

The dried material is pooled in a dry cabinet using nitrogen as an inert atmosphere to reduce relative humidity to less than 1%. The pooled dried material is ground lightly with a motor and pestile.

EXAMPLE I

A portion of the milled dried material is treated with the hydrophobous compounds recited in Table 1 in a 1:10 ratio by weight and passed through a sintered glass filter. The hydrophobous material is evacuated from the cake that forms on the filter. The percent of moisture adsorbed is determined by exposing the material in an environmental chamber to an atmosphere at a relative humidity of 85% at 26° C. for 30 minutes. The material is then stored at 37° C. for 24 hours.

TABLE I

| Runs | Treatment | LIQUID SLURRIES | | | DRIED MATERIALS | | | | Moisture Adsorption (Corrected) % |
|---|---|---|---|---|---|---|---|---|---|
| | | Egg Assay $10^7$ PIU/ml | MTD, hr | Mouse Assay MTD, hr | Egg Assay $10^8$ PIU/gm | MTD, hr After Drying | After Aerosol plus Heat (37° C. - 24 hrs) | Mouse Assay MTD, hr After Drying | After Aerosol plus Heat (37° C. - 24 hrs) | |
| 1. | None | 3.20 | 35** | 178 | 1.30 | 44 | 44 | 150* | 125* | 41 |
| | Butyl Acetate | — | — | — | 1.35 | 43 | — | 190* | — | — |
| 2. | None | 3.08 | 37** | 147** | 1.75 | 45 | 46 | 97 | 162 | 61 |
| | Butyl Acetate | — | — | — | 0.90 | 44 | — | 97 | — | — |
| | Freon 12 | — | — | — | 2.60 | 34** | 37 | 110 | 239* | 23 |
| | Butyl Acetate | — | — | — | 0.75 | 41 | 34 | 127* | 162* | 38 |
| | Freon FC 43 | — | — | — | 1.75 | 38 | 42 | 159* | 592* | 12 |
| | Freon FC 75 | — | — | — | 2.61 | 33** | 47 | 104 | 225* | 12 |
| | Freon FX 74 | — | — | — | 3.52 | 33** | 54* | 108 | 140* | 27 |
| | Methyl Amyl Acetate | — | — | — | 2.36 | 36 | 50* | 102 | 203* | 9 |

TABLE I-continued

| | | LIQUID SLURRIES | | | DRIED MATERIALS | | | | |
| | | | | | | MTD, hr | | Mouse Assay MTD, hr | | Moisture |
| Runs | Treatment | Egg Assay $10^7$ PIU/ml | MTD, hr | Mouse Assay MTD, hr | Egg Assay $10^8$ PIU/gm | After Drying | After Aerosol plus Heat (37° C. - 24 hrs) | After Drying | After Aerosol plus Heat (37° C. - 24 hrs) | Adsorption (Corrected) % |
|---|---|---|---|---|---|---|---|---|---|---|
| 3. | None | 8.50 | 36** | 1.26** | 2.08 | 36 | 43 | 107 | 192* | 38 |
| | Butyl Acetate | — | — | — | 0.74 | 36 | — | — | — | — |
| | Methyl Amyl Acetate | — | — | — | 2.40 | 39 | 39 | 160* | 219* | 34 |
| 4. | None | 3.33 | 49** | 140** | 1.44 | 42 | 49 | 227* | 217* | 38 |
| | Butyl Acetate | — | — | — | 1.14 | 37 | — | — | — | — |
| | Methyl | — | — | — | 1.73 | 42 | 55* | 119 | 222* | 34 |

The runs consisted of a 80% suspension of the chorioallantoic membranes in an aqueous solution stabilized as follows:
1. 2.0% raffinose, 2.0% lactose, 1.2% lysine, 1.2% glutamate, 0.4% isoniazid and 0.4% thiourea;
2. 1.0% raffinose, 1.0% lactose, 0.6% lysine, 0.6% sodium glutamate, 0.2% isoniazid and 0.2% thiourea;
3. 0.5% raffinose, 0.5% lactose, 0.3% lysine, 0.1% isoniazid and 0.1% thiourea; and
4. The solution of 1 above was subjected to trypsinization prior to stabilization.
*above normal
**below normal The hydrophobous compounds utilized did not adversely affect the pock titers or the egg infectivities. However, the mouse infectivity was significantly decreased when butyl acetate and Freon FC 43 was used with the stabilizer of run 2 and when methyl amyl acetate was used with the stabilizer of run 3. The coating of the dry variola virus with the hydrophobous compound did decrease the amount of the moisture absorbed. The dried material obtained by treating the stabilized material of run 2 with methyl amyl acetate was associated with exceptional fine handling properties. The powder flowed freely, was much easier to handle, and did not possess the static charge usually found with dried materials.

EXAMPLE II

Samples of 100 milligrams of the dried variola virus recited in Table II (conditioned as indicated), were exposed to a relative humidity of 10, 60, and 85% for a period of 7.5, 15, 30, 45, 60, 90 and 120 minutes.

was slightly higher than the adsorption of the other 3 products at the higher periods of time. At a relative humidity of 85%, the four dried materials disclose a vast difference in their susceptibility to moisture as shown graphically in FIG. 1. The dried variola virus prepared by non-differential centrifugation, stabilized with 1% lactose, 1% raffinose, 0.6% sodium glutamate, 0.6% lysine, 0.2% isoniazid, 0.2% thiourea and treated with methyl amyl acetate (No. 4), showed the best resistance to the adsorption of moisture.

EXAMPLE III

The materials of Example II above were stored at a temperature of 50° C. for a period of 24 hours following the exposure to air for a period of two hours at a relative humidity of 85%. The infectious qualities of the dried material was then tested on mice (Table III). The dried materials were diluted with water to a concentration of 10-3.

TABLE II

| | MOISTURE ADSORPTION OF DRIED PREPARATIONS | | | | | | | | | |
| | Dried Material | | | | | | | | | |
| NO. | Method of Purification | Stabilizer | Coating | RH in Environmental Chamber, % | Moisture Adsorption at Indicated Time in Minutes, % | | | | | |
| | | | | | 7.5 | 15 | 30 | 45 | 60 | 90 | 120 |
|---|---|---|---|---|---|---|---|---|---|---|---|
| 1 | Deferential Centrifugation | A. | None | 10 | 0 | 0 | 0 | 0 | 0 | 0 | 0 |
| | | | | 60 | 16 | 24 | 28 | 29 | 28 | 29 | 27 |
| | | | | 85 | 15 | 35 | 54 | 59 | 61 | 57 | 60 |
| 2 | None | B. | None | 10 | 3.5 | 3.5 | 7 | 5.4 | 6.6 | 5.5 | 5.8 |
| | | | | 60 | 19 | 24 | 27 | 26 | 32 | 34 | 34 |
| | | | | 85 | 30 | 57 | 73 | 82 | 83 | 80 | 84 |
| 3 | Deferential Centrifugation | C. | None | 10 | 0 | 0 | 0 | 0 | 0 | 0 | 0 |
| | | | | 60 | 20 | 30 | 30 | 32 | 33 | 27 | 28 |
| | | | | 85 | 20 | 31 | 32 | 37 | 37 | 31 | 36 |
| 4 | None | D. | Methyl Amyl Acetate | 10 | 0 | 0 | 0 | 0 | 0 | 0 | 0 |
| | | | | 60 | 24 | 28 | 33 | 29 | 27 | 27 | 23 |
| | | | | 85 | 20 | 23 | 30 | 26 | 26 | 30 | 26 |

The dried material consisted of an 80% suspension of the chorioallantoic membranes stabilized as follows:
A. 2.5% lactose, 2.5% raffinose, 1.5% sodium glutamate, 1.5% lysine, 1.5% dextrin, 0.5% isoniazid, 0.5% thiourea;
B. heart infusion broth:
C. 9.0% Pet skim milk, 0.3% sodium glutamate, 0.3% lysine, 0.3% glycine, 0.1% isoniazid, 0.1% thiourea; and
D. 1% lactose, 1% raffinose, 0.6% sodium glutamate, 0.6% lysine, 0.2% isoniazid, 0.2% thiourea.

At 10% relative humidity, there is no moisture absorbed by the coated product or the two products prepared by differential centrifugation. At 60% relative humidity, there is no significant difference in the moisture adsorption of the four products. However, the absorption of moisture of the control sample (No. 2)

TABLE III

MOUSE INFECTIVITY OF DRIED MATERIAL BEFORE AND AFTER EXPOSURE

| Dried Material NO. | Before Exposure, hr | Mouse MTD, hr After Exposure for Indicated Time in Minutes plus Storage at 50° C. for 24 hours | | | | |
|---|---|---|---|---|---|---|
| | | 7.5 | 15 | 30 | 60 | 120 |
| 1. | 115 | 109 | 120 | 114 | 130 | 158 |
| 2. | 122 | 259 | 420 | 420 | 460 | 465 |
| 3. | 116 | 249 | 267 | 209 | 253 | 256 |
| 4. | 105 | 102 | 120 | 112 | 115 | 99 |

Thus the non-purified chorioallantoic membranes (No. 4), stabilized with 1% lactose, 1% raffinose, 0.6% sodium glutamate, 0.6% lysine, 0.2% isoniazid and 0.2% thiourea were the most resistant to the combined effect of exposure to moisture and moisture plus heat.

The materials herein where subjected to simulated aerosol testing and stress in an environmental chamber, which is the subject of sole co-pending application Ser. No. 367,900, filed May 14, 1964, now U.S. Pat. No. 3,308,558. The above environmental chamber is a simple apparatus utilizing two membrane filter holders, built top-end to top-end. Since dried powders can be exposed in this apparatus to an air stream at any desired relative humidity, it is possible to use this apparatus to determine the effect of humidity upon the viability of the virus, and the relative "wettability of the powder."

Since the dried powder is fluidized in this system, caking is not a problem.

We claim:

1. A process for coating dry variola virus which comprises the steps of:
   (a) chorioallantoic inoculation of the embryo of fertile eggs,
   (b) incubating the eggs for a period of time sufficient to cultivate the virus,
   (c) separating the embryo from the rest of the egg,
   (d) homogenizing the harvested embryo,
   (e) stabilizing the resultant mixture by the addition thereto of a stabilizer comprising the following percent weight per volume: 0.5% to 2.0% lactose; 0.5% to 2.0% raffinose; 0.3% to 1.2% lysine; 0.3% to 1.2% sodium glutamate; 0.1% to 0.4% isoniazid; and 0.1% to 0.4% thiourea.
   (f) pelletizing, freeze-drying, pooling and milling of the stabilized slurry,
   (g) treatment of the milled dried variola material with methyl amyl acetate in a ratio of 1:10 by weight and the agitation thereof,
   (h) filtering the resultant mixture under a vacuum,
   (i) recovering the product.

2. A process in accordance with claim 1 wherein the following stabilizers are in percent weight per volume: 1.0% lactose, 1.0% raffinose, 0.6% lysine, 0.6% sodium glutamate, 0.2% isoniazid and 0.2% thiourea.

* * * * *